United States Patent [19]

Reimann

[11] 4,017,516
[45] Apr. 12, 1977

[54] NOVEL MONOESTERS OF ROSAMICIN

[75] Inventor: Hans Reimann, Wayne, N.J.

[73] Assignee: Schering Corporation, Kenilworth, N.J.

[22] Filed: Oct. 30, 1975

[21] Appl. No.: 627,322

Related U.S. Application Data

[63] Continuation-in-part of Ser. No. 303,903, Nov. 15, 1972, abandoned.

[52] U.S. Cl. .............................. 260/343; 424/279
[51] Int. Cl.² .................................... C07D 315/00
[58] Field of Search ................................... 260/343

[56] References Cited
OTHER PUBLICATIONS

Reimann et al., J.C.S. Chem. Comm., p. 1270 (1972).

Primary Examiner—John M. Ford
Attorney, Agent, or Firm—Carver Joyner; Stephen Coan; Raymond McDonald

[57] ABSTRACT

Described herein are novel monoesters of rosamicin, also known as Antibiotic 67–694. Also described is a process for the preparation of such esters by the selective solvolysis of diester precursors. The monoesters are broad spectrum antibacterial agents but are generally more effective against gram-positive bacteria.

12 Claims, No Drawings

NOVEL MONOESTERS OF ROSAMICIN

This application is a continuation-in-part of copending application Ser. No. 303,903, filed Nov. 15, 1972, now abandoned.

This invention relates to a new class of derivatives of rosamicin and to a process for their preparation. More particularly, this invention relates to 3-monoesters of rosamicin, and to processes for their preparation from 3,2'-diesters of the antibiotic via solvolysis.

DESCRIPTION OF THE PRIOR ART

The novel compounds of this invention are derivatives of Antibiotic 67–694 which is described in Belgian Patent No. 761,922, granted July 21, 1972. Subsequent to the issuance of the Belgian Patent, the antibiotic was given the name "rosamicin". Thus, Antibiotic 67–694 and rosamicin are synonyms. Rosamicin is elaborated by a rosamicin producing strain of *Micromonospora rosaria* which is also described in the aforementioned Belgian Patent.

BACKGROUND OF THE INVENTION

When rosamicin is subjected to mild acylating conditions, it forms monoesters at position 2'. Under more rigorous acylating conditions 3,2'-diesters are formed. Attempted hydrolyses of such diesters to produce 3-monoesters, under the hydrolytic conditions normally used in the art, cause one or more of several reactions to take place, e.g. both acyl functions are removed yielding the unacylated antibiotic, the lactone moiety of the aglycone hydrolyzes to yield an open-chain compound, the glycoside moiety is removed and gross degradation of the aglycone occurs. Generally, two or more of the foregoing reactions take place concurrently thereby giving rise to a plethora of undesired by-products. None of the prior art hydrolytic conditions provide a suitable method for obtaining the desired 3-monoesters. I have discovered a procedure which provides a facile means for preparing the previously unobtainable 3-monoesters of rosamicin.

DESCRIPTION OF THE INVENTION

The compounds of this invention may be described as 3-monoesters of rosamicin having the formula:

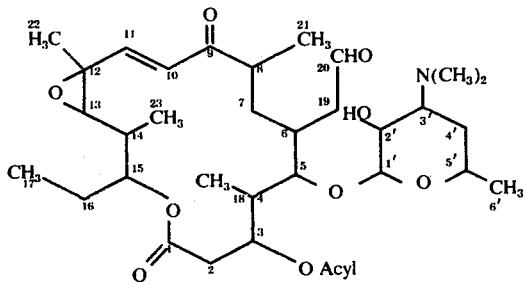

and the pharmaceutically acceptable acid addition salts thereof wherein the acyl function is a

moiety derived from a hydrocarbon carboxylic acid having from 2 to 18 carbon atoms, including straight and branched chain alkyl, cycloalkyl, aryl, aralkyl and dibasic acids.

The compounds of this invention may be prepared by a novel process which comprises selective solvolysis of a 3,2'-diester of rosamicin in a medium comprising a lower alcohol or optionally comprising a water miscible organic solvent or a mixture of up to about 50% of water with such solvent until the 2'-acyl function is selectively removed and isolating the 3-monoester from said medium.

Under the selective solvolysis process of this invention, the 2'-ester is removed without causing cleavage of the lactone ring or any other degradation or rearrangement of the antibiotic macrostructure.

There exist many methods in the art for following the course of the solvolysis; with thin-layer chromatography and mass spectral analysis being preferred. During the course of the solvolysis samples of the reaction mixture are removed at convenient intervals, diluted with a water immiscible solvent, such as ethyl acetate, toluene or the like, washed with water, dried and subjected to thin layer chromatography on silica gel in a suitable solvent system, such as chloroform-methanol-9:1 (v/v). For comparison, samples of the starting compound (i.e. the 3,2'-diester), rosamicin and the corresponding 2'-monoester are also chromatographed. Disappearance of the 3,2'-diester spot from the test sample combined with the appearance of a material whose migration is different from that of the compounds spotted for comparison and slower than (more polar) the 3,2'-diester starting compound indicates that the reaction is substantially complete.

Isolation of the 3-monoester may be effected by the numerous methods generally used in the art. For example, it may be accomplished by diluting the reaction medium with water followed by extraction with a water immiscible solvent and removal of the solvent by distillation. When this technique is used, it is preferred that the solvent be removed in vacuo. Another method for isolating the products of this invention is by concentrating the reaction mixture to a residue or to a crystalline mass. Other methods may be employed with efficacy to effect the isolation, provided such methods are not sufficiently harsh to cause substantial degradation of the 3-monoester product.

The term acyl denotes residues derived from hydrocarbon carboxylic acids having 2 to 18 carbon atoms, and may be saturated, unsaturated, straight chain, or branched chain, aliphatic, cyclic, cyclic-aliphatic, aromatic, aryl-aliphatic, or alkyl-aromatic, and may be substituted by 1 or more members of the group consisting of hydroxy, $C_1$ to $C_5$ alkoxy, halogen or trifluoromethyl. Typical acyl groups are those derived from such hydrocarbon carboxylic acids as acetic, propionic, pivalic, butyric, isobutyric, valeric, iso-valeric, caproic, caprylic, capric, undecylic, lauric, myristic, palmitic, stearic, phenoxyacetic, β-chloropropionic, benzoic, toluic, chlorobenzoic, phenylacetic, phenylpropionic, acrylic, sorbic, linolenic, succinic, tartaric, adamantane carboxylic and phthalic acids.

Preferred acyl groups are those derived from hydrocarbon carboxylic acid having from 2 to 7 carbon atoms such as acetic, propionic, pivalic, benzoic, acrylic, succinic, tartaric and malonic acids.

Acid addition salts of the 3-monoesters disclosed herein may be prepared by procedures generally used in the art. It is preferred that the salts be prepared by treating the 3-monoester with a stoichiometric quantity of acid (or a slight excess thereof) in an aqueous medium followed by lyophilization of the resulting solution. Exemplary of acids suitable for preparing such salts are hydrochloric, sulfuric, phosphoric, acetic, citric, propionic, maleic, benzoic, tartaric, monopotassium phosphoric, octanoic, valeric, decanoic, stearic, lauryl sulfuric, octadecyl sulfuric, and the like.

The solvolysis process of this invention may be effected in water miscible organic solvents such as cyclic ethers, ketones, lower alkyl tertiary amides and alcohols, preferably lower molecular weight alcohols having 1–4 carbon atoms. Exemplary of such solvents are dioxane, tetrahydrofuran, acetone, methyl ethyl ketone, dimethylformamide, methanol, ethanol, propanol or the like. In those instances wherein the reaction is effected in a solvent other than a lower molecular weight alcohol, from about 5% to about 50% by volume of water is added to the reaction medium. In those instances wherein the reaction is effected in a lower molecular weight alcohol, water need not be added but the addition of up to about 50%, preferably about 20%, water usually facilitates the hydrolysis. The reaction may be effected at temperatures ranging from about 0° C to about 100° C, preferably at about ambient temperature. The solvolysis reaction may be effected in about 2 to about 72 hours. It is preferred that the reaction be performed at ambient temperatures in a medium comprising a low molecular weight alcohol, water and the 3,2'-diester. It is noteworthy, however, that when the reaction is effected under the foregoing conditions, the solvolysis proceeds only to the 3-monoester stage, there being substantially no rosamicin produced.

The compounds of this invention exhibit substantial in vitro antibacterial activity against pathogenic species of gram-positive and gram-negative microorganisms. Representative of the gram-positive group are species of Staphylococcus, Streptococcus, Bacillus and Diplococcus. Representative of the gram-negative group are species of Proteus, Pseudomonas, Escherichia and Klebsiella. Thus, they may be used to inhibit or to eradicate susceptible microorganisms in such places as hospitals especially in bathrooms and on objects that are particularly susceptible to contamination, e.g. examining tables, bathtubs, sinks, surgical instruments, or the like. These antibacterial agents are of substantial value when used in conjunction with solutions of soaps and detergents for cleaning contaminated surfaces.

The compounds of this invention also exhibit substantial in vivo antibacterial activity. Thus, they may be used to treat mammals infected with susceptible microorganisms. For example, rosamicin 3-propionate has a $PD_{50}$ (mg./kg.) in male CF-1 mice against a variety of strains of Staphylococcus aureus, and Streptococcus pyogenes of 2.5 – 25 and 25, respectively, by subcutaneous administration 1 hour after intraperitoneal infection. Untreated, infected mice generally die 18 – 24 hours after infection. The treated survivors are determined 48 hours after infection.

Acute intraperitoneal and subcutaneous toxicities of rosamicin 3-propionate in terms of $LD_{50}$ as determined in CF-1 mice by standard test methods are 550 mg./kg. and 750 mg./kg., respectively.

For in vivo application, the compounds of this invention may be administered topically, orally or parenterally, preferably in admixture with suitable pharmaceutical excipients. Although the precise dose to be administered in any given dosage form depends upon many factors such as the stage and severity of the invention, the susceptibility of the infecting organism to the antibiotic and the individual characteristics of the mammalian species being treated, it is generally preferred that the antibiotic be administered at from about 5 mg. to about 20 mg. per kilogram of body weight per day divided into 2 to 4 equal doses. Where warranted larger or smaller doses may be administered, the precise regimen to be followed being left to the discretion of the practitioner. However, a typical pharmaceutical formulation for administering compounds of this invention is as follows:

| Capsule | |
|---|---|
| Rosamicin 3-propionate | 250.00 mg. |
| Lactose | 248.75 mg. |
| Magnesium Stearate | 1.25 mg. |
| | 500.00 g. |

Procedure

1. Blend the antibiotic and the lactose.
2. Add the magnesium stearate and mix.
3. Fill capsule.

The starting diester compounds of the following specific examples may be prepared as described in the above-cited Belgian Pat. No. 761,922 or as described in Preparations 1 and 2 below.

PREPARATION I

Rosamicin 3,2'-Dipropionate

Dissolve 1.0 g of rosamicin in 12 ml. of pyridine and add 1.7 ml. of propionic anhydride. Stir the mixture at room temperature for 5 days, then concentrate to a residue under reduced pressure. Triturate the residue with 5% aqueous ammonium hydroxide and isolate the resulting solid by filtration. Purify the product by chromatography on silica gel using chloroform as the eluant. Combine fractions containing the desired product and concentrate to a residue of the desired product. m.p. 85° – 87° C, $[\alpha]_D = -18°$ (C=0.3% ethanol), $\lambda_{max}^{CH_3OH}$ 240 m$\mu$ ($\epsilon$ = 14,000).

PREPARATION II

Rosamicin 3-Benzoate-2'-Acetate
Rosamicin-2'-Acetate

A. Dissolve 1.0 g. of rosamicin in 10 ml. of dry acetone and add 0.17 ml. of acetic anhydride. Stir the mixture at room temperature for 4 hours, then slowly and with stirring add 1.2% ammonium hydroxide to precipitate the product. Filter the resulting precipitate, wash with dilute aqueous acetone, wash with water and dry. Crystallize from aqueous acetone to obtain the desired product. m.p. 112°–116° C, $[\alpha]_D^{20} = -25°$ C (C = 0.3%, ethanol)

Rosamicin 3-benzoate-2'-Acetate

B. Stir a solution of 300 mg. of rosamicin 2'-acetate and 0.5 ml. of benzoyl chloride in 10 ml. of pyridine at room temperature for 48 hours. Concentrate the solution to a residue under reduced pressure and triturate with ammonium hydroxide. Dissolve the solids in ethyl acetate, wash with sodium bicarbonate solution, with saturated sodium chloride and dry over sodium sulfate. Concentrate under reduced pressure to a residue of the desired compound. m.p. 76°–78° C, $[\alpha]_D = -12°$ (C=0.3% ethanol).

By substituting equivalent quantities of other hydrocarbon carboxylic acid anhydrides or chlorides and by following the procedures of the Preparations set forth above, the corresponding rosamicin 3,2'-diesters may be prepared.

EXAMPLE 1

Rosamicin 3-propionate potassium dihydrogen phosphate salt

A. Rosamicin 3-propionate

Dissolve 4.6 g. of rosamicin 3,2'-dipropionate in 40 ml. of a mixture consisting of 32 ml. of methanol and 8 ml. of water. Heat the resulting solution at reflux for about two hours. Concentrate the solution under reduced pressure to a residue consisting of rosamicin 3-propionate, m.p. 93°–95° C $[\alpha]_D^{26}$ –20° ethanol, $\lambda_{max}^{MeOH}$ 240 nm $\epsilon = 13,200$.

B. Rosamicin 3-propionate potassium dihydrogen phosphate salt

Dissolve 10.7 mg. of potassium dihydrogen phosphate in 10 ml. of water and add 50 mg. of rosamicin 3-propionate. Stir the mixture for about one hour at room temperature (about 25° C) and filter the solution to remove traces of insoluble matter. Lyophilize the filtrate to obtain rosamicin 3-propionate potassium dihydrogen phosphate salt, melting 98°–104° C, $[\alpha]_D^{26}$ –15.2 (H$_2$O) (C=0.3), $\lambda_{max}^{MeOH}$ 238 nm $\epsilon = 13,000$.

Other non-toxic pharmaceutically acceptable acid addition salts of the rosamicin 3-monoesters may be prepared by substantially the process set forth in Example 1B. Exemplary of such salts are those formed with such acids as hydrochloric, sulfuric, citric, acetic, propionic, tartaric, maleic, benzoic, cyclopropanecarboxylic, adamantanecarboxylic, stearic acid and the like.

EXAMPLE 2

Rosamicin 3-acetate

Dissolve 185 mg. of rosamicin 3,2'-diacetate in 8.0 ml. of 80% aqueous methanol and keep at room temperature for 4 hours. Concentrate to a residue, dissolve the latter in chloroform, filter through 1.5 g. of silica gel and concentrate to a residue under reduced pressure. Dissolve the residue in chloroform and crystallize from chloroform-hexane to obtain the compound of this example as a chloroform solvate, m.p. 108°–110° C. Recrystallize from chloroform-hexane and dry in vacuo at 60° to obtain the solvent-free compound of this example, m.p. 145°–147°, $\lambda_{max}^{MeOH}$ 239 nm $\epsilon = 14,000$.

EXAMPLE 3

Rosamicin 3-benzoate

Keep a solution of 40 mg. of rosamicin 3,2'dibenzoate in one ml. of 80% aqueous methanol at room temperature for 40 hours. Concentrate to a residue under reduced pressure. Dissolve the residue in methanol and pour into ice water. Isolate the resulting precipitate by filtration, wash with water and dry to obtain the compound of this example, m.p. 111°–115°, mass spectrum M $^+$ 685.

EXAMPLE 4

Rosamicin 3-valerate

A: Rosamicin 2'-acetate-3-valerate

Stir a solution of 623 mg. of rosamicin 2'-acetate and 0.5 ml. of valeric anhydride in 10 ml. of pyridine at room temperature for 24 hours. Concentrate to a residue under reduced pressure and triturate the residue with ammonium hydroxide. Extract the resulting mixture with ethyl acetate and wash the extracts with sodium bicarbonate and water. Concentrate the organic solution to a residue of the above-named diester, m.p. 85°–86°, mass spectrum M $^+$ 707.

B. Rosamicin 3-valerate

Stir a solution of 625 mg. of the compound of Step A in 20 ml. of 75% aqueous methanol at room temperature for 4 hours. Replace the solvent with ethyl acetate, wash with sodium bicarbonate and concentrate to a residue to obtain rosamicin 3-valerate, m.p. 104°–105°, $[\alpha]_d^{26}$ – 39° (0.3% ethanol).

EXAMPLE 5

Rosamicin 3-propionate

A: Dissolve 35 mg. of rosamicin 3,2'-dipropionate in 0.5 ml. of 92% aqueous methanol and allow the solution to stand at room temperature for 18 hours. Concentrate the solution under reduced pressure to give a residue consisting of the compound of this example.

B: Dissolve 5 mg. of rosamicin 3,2'-dipropionate in 0.5 ml. of 95% ethanol. Keep the solution at about 25° C for 72 hours. Concentrate the solution under reduced pressure to a residue to obtain rosamicin 3-propionate.

C: Dissolve 10 mg. of rosamicin 3,2'-dipropionate in 0.5 ml. of a solvent mixture consisting of 80% tetrahydrofuran and 20% water. Keep the solution at about 25° C for about 72 hours. Concentrate the solution under reduced pressure to a residue to obtain rosamicin 3-propionate.

D: Repeat C using a solvent mixture consisting of 80% acetone and 20% water to obtain rosamicin 3-propionate.

In a similar manner by subjecting rosamicin 3,2'-diesters other carboxylic acids by the process of the foregoing examples, the corresponding rosamicin 3-monoesters may be prepared. Exemplary of such other acids are the following: butyric, pivalic, iso-valeric, caproic, caprylic, capric, undecylenic, lauric, myristic, palmitic, stearic, phenoxyacetic, β-chloropropionic, chlorobenzoic, toluic, phenylacetic, acrylic, sorbic, succinic, tartaric, malonic acids.

I claim:

1. A process for preparing a 3-monoester of rosamicin which comprises solvolyzing a 3,2'-diester of rosamicin in a medium comprising a water miscible organic solvent containing from about 5% to about 50% water by volume, at from about 0° C to about 100° C, continuing said solvolysis for from about ¼ to about 72 hours and isolating the 3-monoester from said medium.

2. A process according to claim 1 wherein the solvolysis is conducted at from about 0° C to about 100° C for from about ½ to about 72 hours in a medium comprising a lower molecular weight alcohol and water in a ratio of from about 5% to about 50% by volume, continuing said solvolysis until the 2'-acyl function is selectively removed and isolating the 3-monoester from said medium.

3. A process of claim 2 wherein the solvolysis is conducted at about 65° C in a medium consisting of an alcohol and water in a ratio by volume of about 4 to 1 for about 2 hours.

4. A process according to claim 3 wherein the solvolysis is conducted at about 65° C in a medium consisting of methanol and water wherein the water is present at about 20% by volume of the methanol, continuing said solvolysis for about 2 hours and isolating the 3-monoester from said medium.

5. A compound of the group consisting of 3-monoesters of rosamicin having the formula:

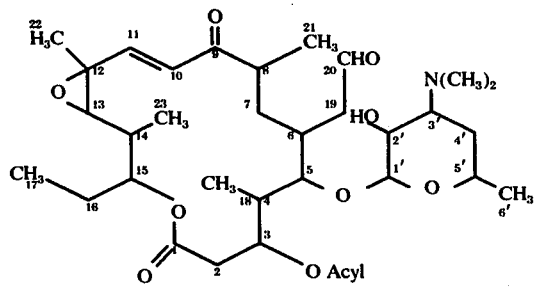

and the pharmaceutically acceptable acid addition salts thereof wherein the acyl function is a

moiety derived from a hydrocarbon carboxylic acid having from 2 to 18 carbon atoms, consisting of straight and branched chain alkyl, cycloalkyl, aryl, aralkyl and dibasic acids.

6. A compound of claim 5, said compound being a 3-monoester of rosamicin wherein said ester is derived from a straight chain hydrocarbon carboxylic acid.

7. A compound of claim 5, said compound being a 3-monoester of rosamicin wherein said ester is derived from an aryl hydrocarbon-carboxylic acid.

8. A compound of claim 6, said compound being a 3-monoester derived from a hydrocarbon carboxylic acid having 2 carbon atoms, said compound being rosamicin 3-acetate.

9. A compound of claim 6, said compound being a 3-monoester derived from a straight chain hydrocarbon carboxylic acid having 3 carbon atoms, said compound being rosamicin 3-propionate.

10. A compound of claim 6, said compound being a 3-monoester derived from a straight chain hydrocarbon carboxylic acid having 5 carbon atoms, said compound being rosamicin-3-valerate.

11. A compound of claim 7, said compound being a 3-monoester derived from an aryl hydrocarbon carboxylic acid having 7 carbon atoms, said compound being rosamicin-3-benzoate.

12. A pharmaceutically acceptable acid addition salt of the compound of claim 9, said compound being rosamicin-3-propionate potassium dihydrogen phosphate.

* * * * *